United States Patent
Moreau et al.

(10) Patent No.: US 6,472,506 B1
(45) Date of Patent: Oct. 29, 2002

(54) POLYSACCHARIDE-PEPTIDE-CONJUGATES

(75) Inventors: Monique Moreau, Lyons (FR); Noëlle Mistretta, Saint-Bel (FR)

(73) Assignee: Aventis Pasteur S.A. (FR)

( * ) Notice: Subject to any disclaimer, the term of this patent is extended or adjusted under 35 U.S.C. 154(b) by 0 days.

(21) Appl. No.: 09/155,077

(22) PCT Filed: Jan. 21, 1998

(86) PCT No.: PCT/EP98/00654

§ 371 (c)(1),
(2), (4) Date: Nov. 4, 1998

(87) PCT Pub. No.: WO98/31393

PCT Pub. Date: Jul. 23, 1998

(30) Foreign Application Priority Data

Jan. 21, 1997 (EP) .............................. 97100884

(51) Int. Cl.[7] ........................ A61K 38/14; A61K 51/00; C07K 1/00

(52) U.S. Cl. .................... 530/322; 530/395; 530/402; 530/403; 424/1.73

(58) Field of Search ................ 530/395, 402, 530/403, 322; 424/1.73

(56) References Cited

U.S. PATENT DOCUMENTS 4,695,624 A * 9/1987 Marburg et al. ............. 530/395

FOREIGN PATENT DOCUMENTS

| EP | 0186576 | 7/1986 |
| EP | 0326111 | 8/1989 |
| EP | 0471453 | 2/1992 |

OTHER PUBLICATIONS de Velasco et al. *Infect. Immun.* 63, 961 (1995).

* cited by examiner

Primary Examiner—Hankyel T. Park
(74) Attorney, Agent, or Firm—McDonnell Boehnen Hulbert & Berghoff

(57) ABSTRACT

The invention relates to a polysaccharide-peptide conjugate wherein the polysaccharide is advantageously immunogenic, which comprises a polysaccharide chain composed of repeat units and a plurality of peptide moieties, each moiety containing a cysteine residue and being covalently attached at random along the polysaccharide chain, through an indirect bond being achieved through either a linker or a spacer-linker moiety provided that the spacer entity of the spacer-linker moiety is linked to the amino, hydroxyl or carboxyl group of the polysaccharide. To this end a useful linker may be, e.g., N-(γ-maleimidobutyrloxy)succinimide ester. Such a conjugate may typically exhibit a "Rake" configuration. Conjugation processes are also disclosed. Conjugates of the invention are in particular useful in the vaccinal field to elicit a protective long term immune response against a pathogenic microorganism from which the Immunogenic polysaccharide is derived.

20 Claims, 1 Drawing Sheet

SEQUENCE LISTING

<160> NUMBER OF SEQ ID NOS: 1

<210> SEQ ID NO 1
<211> LENGTH: 105
<212> TYPE: PRT
<213> ORGANISM: Artificial/Unknown
<220> FEATURE:
<221> NAME/KEY: UNSURE
<222> LOCATION: (1)..(105)
<223> OTHER INFORMATION: Synthetic 105 mer peptide

<400> SEQUENCE: 1

Cys Leu Tyr Tyr Lys Asn Tyr Arg Tyr Tyr Ala Leu Lys Ser Gly Gly
1               5                   10                  15

Ser Val Asn Ala Pro Met Pro Glu Asn Gly Gln Thr Glu Asn Asn Asp
            20                  25                  30

Trp Ile Leu Met Gly Ser Thr Gln Glu Glu Ala Lys Lys Asn Ala Met
        35                  40                  45

Asn His Lys Asn Asn Gln Arg Ile Ser Gly Phe Ser Gly Phe Phe Gly
    50                  55                  60

Glu Glu Asn Gly Lys Gly His Asn Gly Ala Leu Asn Leu Asn Phe Asn
65                  70                  75                  80

Gly Lys Ser Ala Gln Asn Arg Phe Leu Leu Thr Gly Gly Thr Asn Leu
                85                  90                  95

Asn Gly Lys Ile Ser Val Thr Gln Gly
            100                 105

POLYSACCHARIDE-PEPTIDE-CONJUGATES

FIELD OF THE INVENTION

The present invention relates to a polysaccharide peptide conjugate and a process for making it. In a particular embodiment of the invention, the conjugate uses bacterial or fungal polysaccharides and thus can be useful for vaccine purposes.

BACKGROUND OF THE INVENTION

Polysaccharides constitute a broad family of polymeric molecules which are useful in various technical fields. In some cases, they require to be coupled to a polypeptide, e.g. protein or peptide. For example, polysaccharides are used in diagnosis or purification technics as a matrix medium for peptide reagents. Non-immunogenic polysaccharides such as dextran, are also useful to present small peptides, to the immune system as described in EP 326 111. Indeed, peptides have to be linked to protein carriers or have to be administered with an adjuvant, the most commonly used adjuvants being aluminium compounds. However, small peptides mixed, adsorbed or precipitated with these adjuvants may be hindered by the aluminium gel and therefore, not available to the immune system. To overcome this problem, EP 326 111 teaches that peptides may be conjugated to non-immunogenic polysaccharides. Such conjugates, in the presence of aluminium compounds, are able to elicit an immune response against the peptide moiety.

In the vaccinal field, it is also highly interesting to conjugate polypeptides e.g., peptide or protein, to immunogenic polysaccharides, this once pursuing an immune response to the polysaccharides. Indeed, capsule and cell wall of bacteria (and also cell wall of fungi) are essentially constituted by polysaccharides composed of very specific repeat units that bear epitope motives that are usually not found in mammals and can mediate immunogenicity. Therefore, polysaccharides e.g., capsular polysaccharides have been already used as vaccines against bacterial diseases such as meningitis, pneumonia and typhoid fever.

However, there is a major problem when using polysaccharides as vaccines. Although they have been proven immunogenic i.e., in other words, they elicit an immune response when administered as such to a mammal, even if this response may be poor, they are specific in that they belong to the small number of antigens that are able to induce B-cells production without help from T-cells. Accordingly, they are called T-independent.

The immune response induced by T-independent antigens is characterized by a number of features, among which:

(i) The primary response is weaker and earlier than the response to T-dependent antigens;

(ii) The antibody response does not mature into high IgG production, with affinity increase, as observed with T-dependent antigens;

(iii) The immune memory corresponding to T-independent antigens is poor and thus, as the immune memory is the key of the secondary immune response that constitutes the basis of the vaccination principle, a T-independent antigen is a poor antigen for inducing a long term protective immune response; and (iv) Infants are unable to respond to polysaccharides before one or two years of age.

In order to induce a secondary immune response, T-independent antigens require to be covalently coupled to a carrier protein such as diphtheria or tetanus toxin, which give the antigen the T-dependent character. The conjugate thereof may then be complemented with an adjuvant such as an aluminium compound or the complete or incomplete Freund's adjuvant (these two latter, exclusively for use in mammals other than humans), so that the immune response is enhanced (adjuvant effect).

By the term "carrier" is meant a molecule that, when covalently linked to an antigen e.g. a polysaccharide, is capable of promoting a T-dependent response to the antigen. Such a response is shown upon a vaccination scheme comprising at least two injections of the antigen-carrier conjugate, at days, weeks or months apart (priming and booster). Upon the first infection (priming), a weak antibody response is shown, while upon the booster injection, the antibody response is elicited at a high level. Such a magnified response is not to be seen with the negative control constituted by the unconjugated antigen.

Various conjugation methods are already available in the art. Polysaccharide functional groups that are commonly involved, may be amino, carboxyl or hydroxyl groups located along the chain or aldehyde groups either terminal or along the chain. Polypeptide functional groups that are usually involved, may be amino or carboxyl groups, terminal or present on the amino acid side chains or even thiol groups.

In a general manner, polysaccharide conjugates may exibit three types of structure depending upon the location of functional groups of both polysaccharide (either along the chain or at the end) and carrier, that are involved in the linkage. These types of structure are called for ease of description, "Sun" or "Ear", "Rake" and "Lattice" types. They are illustrated in FIG. 1, wherein (A), (B) and (C) respectively stand for "Sun" (neoglycoconjugate), "Rake" and "Lattice" types.

In the "Sun" type, a polysaccharide is attached to a protein or peptide through a reactive group exclusively located at an extremity of the polysaccharide chain. Usually, this involves a carbonyl group located at the reductive end of the polysaccharide chain. Several polysaccharide chains may be attached onto the protein, the attachement usually involving an amino group carried by e.g., a lysine residue. Such conjugates are also defined as neoglycoconjugates. As a matter of example, a conjugate of this type is achieved in Alonso de Velasco et al, Infect. Immun. (1995) 63: 961, Paradiso et al, Vaccine Research (1993) 2 (4): 239, and Jennings U.S. Pat. No. 4,356,170.

In the "Rake" type, peptides are attached along the polysaccharide chain. An example of this type is provided in Lett et al, Infect. Immun. (1994) 62: 785, and more appropriately, Lett et al, Infect. Immun. (1995) 63: 2645 and Könen-Waisman et al, J. Immunol. (1995): 5977. Attachement involves the amino group carried by the single lysine residue internal to the peptide sequence and/or the terminal amino group.

In the "Lattice" type, the protein and the polysaccharide are cross-linked. This is made possible due to the fact that a protein rather than a peptide is used (usually amino or acid groups located along the protein) and that reactive groups located along the polysaccharide chain are involved. A conjugate of this type is described in Anderson U.S. Pat. No. 4,673,574. Schneerson et al, J. Exp. Med. (1980) 152: 361 also describes a conjugation method leading to a "Lattice" type" It uses CNBr and as a linker, adipic acid dihydrazide (ADH). Hydroxyl groups present all along the polysaccharide chain and side chain amino groups of the protein are involved.

Each of these structures may be achieved according to a variety of conjugation processes. The bound may be a direct bound as in Anderson U.S. Pat. No. 4,673,574, Jennings U.S. Pat. No. 4,356,170, Lett et al or Könen-Waisman et al. The bound may also be an indirect bound in that a linker molecule is used as illustrated by Schneerson et al. Additional to a linker, a spacer may also be used as described in Alonso de Valesco et al or Paradiso et al (for the pneumococcal polysaccharide). Various functional groups present on polysaccharide, protein, linker and optionally, spacer may be involved.

Some of the prior art reference cited above are presented with further details as follows:

In Alonso de Velasco et al, the carrier is a peptide of about 20 amino acid residues that comprises a single cysteine residue at either end. *Streptococcus pneumoniae* 17F polysaccharide is first derivatized at the reductive end by reductive amination with diaminopropane in the presence of $NaCNBH_3$. Then the derivatized polysaccharide is bromoacetylated with N-succinimidyl bromoacetate as a linker and the polysaccharide so activated is coupled to the thiol group of the single N- or C-terminal cysteine residue of the peptide. A single-ended conjugate is thus obtained.

In Lett et al (1994), *S. mutans* or *Saccaromyces cerevisiae* polysaccharide are first oxidized with periodate so as to create aldehyde groups all along the polysaccharide chain. Then the oxidized polysaccharide is directly coupled by reductive amination to a peptide, in the presence of $NaCNBH_3$.

In Paradiso et al, two polysaccharides are used: a pneumococcal polysaccharide and the polyribitol phosphate (PRP) of *Haemophilus influenzae*. Upon acidic hydrolysis of the pneumococcal polysaccharide, an aldose group is first created at the end of the polysaccharide chain. Amino groups are then added at the end of the chain upon reductive amination with diaminomethane in the presence of pyridine borane. The derivatized polysaccharide is activated with succinimidyl diester of adipic acid and coupled to amino groups of protein or peptide: Turning to PRP, this latter is first submitted to oxidative cleavage using periodate. Aldehyde groups are thus created at both ends. Oxidized PRP is then coupled to the amino groups of protein and peptide. In both cases, a "Sun" structure is created.

In Könen-Waisman et al, the Vi polysaccharide and peptides (none of which contains a cysteine residue) or proteins are directly coupled together in the presence of (3-dimethylaminopropyl)-3-ethyl carbodiimide hydrochloride (EDAC):carboxyl groups of the polysaccharide and amino groups of the protein or peptides are involved in the conjugation. As a result, a "Lattice" structure is created when the protein is used. When peptides are used, the structure depends upon the number of amino acid residue that bears amino groups. It may be either a simple "Lattice" structure or a "Rake" structure.

As may easily be understood, when conjugation involves functional groups present all along the polysaccharide chain, this leads to a cross-linked conjugate if the carrier is a protein (several amino or carboxyl groups on the protein are available for attachment). If the polypeptide carrier contains a single attachment site (this situation is very frequent when it is small enough), the conjugate thereof exhibits a "Rake" structure (that may also be achieved if the polypeptide contains a few attachment sites and the conjugation carried out under close, uneasy control so that a single functional group on the polypeptide is reacted). When the conjugation method uses carboxyl or amino groups of a naturally-occurring polypeptide (or a fragment therof), this latter shall pretty small in order to get a "Rake" structure, since carboxyl or amino groups are frequently encountered on polypeptides.

SUMMARY OF THE INVENTION

It has now been found a novel conjugation method that may easily produce a "Rake" structure, while using the thiol group of a cysteine residue. Since cysteine residues are less frequent than lysine and aspartic acid, this method is therefore suitable for conjugating larger peptides.

As carrier, peptides have some advantages over proteins since they can easily be purified when biologically produced, or synthesized and therefore, are purer and more defined. Contrarily to carrier proteins which may also have detrimental properties (toxicity), peptides may be derived from those proteins so as to exhibit the carrier property only.

However, polysaccharide-peptide conjugates known in the art are less immunogenic than their polysaccharide-protein counterparts and definitively require adjuvantation. Surprisingly, polysaccharide-peptide conjugate made by the novel method have good immunogenicity. One of the reasons for this lies within the fact that the peptide moiety has a sufficient size.

Therefore, the present invention relates to a polysaccharide-peptide conjugate wherein the polysaccharide is advantageously immunogenic, which comprises:

(i) a peptide moiety having at least six amino acid residues, at least one of which being a cysteine residue;

(ii) a polysaccharide chain comprising at least four repeat units; and (iii) a linker moiety bound to the thiol group of the cysteine residue and bound to (a) the native amino, hydroxyl or carboxyl groups of the polysaccharide chain or (b) amino groups created upon hydrolysis of the native N-acyl groups of the polysaccharide chain or (c) functional groups introduced on the polysaccharide chain upon derivatization with a spacer moiety bound to the native amino, hydroxyl or carboxyl groups of the polysaccharide chain.

Since the native amino, hydroxyl or carboxyl groups are found in the repeat units and therefore are present all along the polysaccharide chain, a conjugate of the invention typically exhibits a rake structure as described herein above. Accordingly, an alternative and equivalent definition for the conjugate of the invention may be provided as follows.

Said otherwise, a conjugate of the invention comprises a polysaccharide chain composed of repeat units and a plurality of peptide moieties, each moiety containing a cysteine residue and being covalently attached at random along the polysaccharide chain, through an indirect bound involving the thiol group of the cysteine residue and an amino, hydroxyl or carboxyl group of the polysaccharide, said indirect bound being achieved through either a linker or a spacer-linker moiety provided that the spacer entity of the spacer-linker moiety is linked to the amino, hydroxyl or carboxyl group of the polysaccharide.

DETAILED DESCRIPTION OF THE INVENTION

Figure 1A:
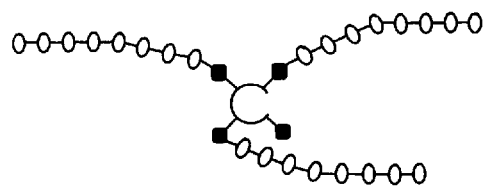
FIGS. 1A, 1B and 1C are schematic representations of the "Sun" (neoglycoconjugate), "Rake" and "Lattice" types of polysaccharide conjugate structure, respectively.
Figure 1B:
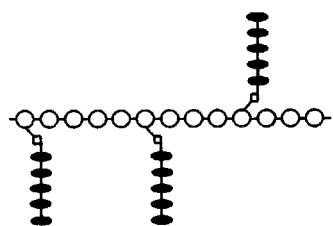
Figure 1C:
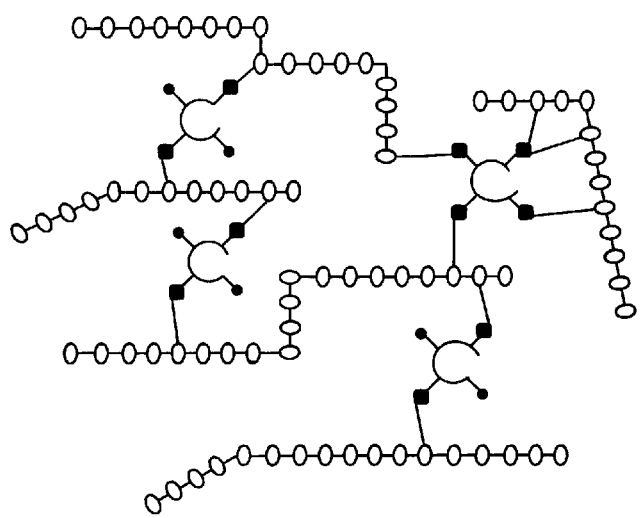

By "peptide" is meant an amino acid chain having at least 6 and advantageously no more that about 200 amino acid residues. The peptide advantageously contains at least 10, preferably at least about 15, more preferably at least about 20 amino acid residues. It advantageously contains at most about 150, preferably at most about 100, or at most about 50 amino acid residues. A preferred peptide contains from about 50 to 150 amino acid residues.

For use in the present invention, the peptide may contain one or several cysteine residues. Cysteine residues provide for the attachment of the linker to the peptide. The use of a cysteine residue for the coupling enhances the selectivity of the coupling as the amount of cysteine residues in a peptide is usually low. Cysteine residue(s) may be located at either end of the peptide or be internal to the peptide chain, provided that attachment at this site does not interfere with the structure and the properties of the peptide. Irrespective of the cysteine amount, it is preferred that one cysteine residue be located at the N- or C-terminal end.

More preferably, the peptide contains two cysteine residues, each being located at one end, or a single cysteine residue located at either end; this latter alternative being most preferred.

The whole amino acid sequence of the peptide may naturally occur as such or as part of a larger polypeptide. It may also be constituted by a naturally-occurring sequence that is extended at the N- or C-terminal end or both ends by an additional cysteine residue.

For use as a carrier in vaccine conjugate, the peptide advantageously contains at least one T-cell dependent epitope and will therefore allow the development of a protective immune response against the polysaccharide that is a T-dependent antigen, upon administration of the conjugate to e.g. a mammal.

For use in the present invention, the peptide may be chemically synthesized or produced by recombinant means. Either method can be achieved conventionally.

A conjugate of the invention may comprise a single peptide; in this case the peptide moieties present all along the polysaccharide chain are identical to each other. It may also comprises several peptides, e.g. bearing different epitopes. A limited number of peptides is however preferred: no more than 6 and more preferably 2 or 3. While a first peptide bears a T-dependent epitope, a second peptide may bear a B-epitope.

Polysaccharides used in conjugates of the present invention may be of any kind. In one embodiment of the invention, conjugates are made for vaccine purposes and therefore the appropriate polysaccharides include capsular polysaccharides, polysaccharides derived form lipopolysaccharides (LPS or LOS) of Gram-negative bacteria cell-wall, such as the O-specific side chain, and also fungal cell-wall polysaccharides. For example, polysaccharides may derive from bacteriae including Pseudomas, such as *P. aeruginosa*, Staphylococci, Streptococci, particularly *S. pneumoniae*, Klebsiellae, e.g. *K. pneumoniea*, Salmonellae, e.g. *S. typhi* and *paratyphi*, Escherichia coli $K_1$, $K_{100}$, 0157:H7, Neisseriae, e.g. *N. meningitidis*, Shigellae, e.g. *S. dysenteriae, somnei* and *flexneri*, Haemophilus, e.g. *H.influenzae* type b, and from fungi such as Catidida, *Cryptococcus neoformans*, and Hansenula.

Polysaccharides are composed of repeat units. For use in conjugates of the invention, a polysaccharide comprises at least 4 repeat units preferably up to 3,000. Especially for use as a vaccine ingredient, a polysaccharide is preferably composed of 4 to 1,000 repeat units, more preferably of 7 to 700 repeat units most preferably of 50 to 200 repeat units.

A repeat unit is characteristic of a given polysaccharide and thus the composition and molecular weight of the repeat unit greatly vary from a polysaccharide to another. For example, while the repeat unit of most capsular polysaccharides comprises hydroxyl and carboxyl groups, some of them contain amino groups (e.g. *Streptococcus pneunomiae* serotype 1), others do not (e.g. *Streptococcus pneunomiae* serotype 14); some of them contain N-acetyls (e.g. *Streptococcus pneunomiae* serotype 14), others do not (e.g. *Streptococcus pneumoniae* serotype 6B). Also as a matter of example, the molecular weight of capsular polysaccharides of *Streptococcus pneunomiae* types 3 and 4 are respectively 360 and 847. Thus, there is no general correspondence between the amount of repeat units and the molecular weight of the polysaccharide, that may be globally applied, irrespective of the polysaccharide composition. However, one may independently indicate that a polysaccharide for use in the present invention has a preferred molecular weight in the average range of 10,000 to 500,000. The molecular weight of a polysaccharide is always expressed as a mean value, since a polysaccharide is constituted by a population of molecules of heterogenous size.

Polysaccharides may be either chemically synthesized or purified from a natural source, if this does exist, according to conventional methods. For example, in the case of bacterial or fungal polysaccharides, these latter may be extracted from the microorganisms and treated to remove the toxic moieties, if necessary. A particularly useful method is described by Gotschlich et al, J. Exp. Med. (1969) 129: 1349.

Polysaccharides may be used as synthesized or purified. They may be also depolymerized prior use. Indeed, native capsular polysaccharides usually have a molecular weight superior to 500,000. When it is preferred to use capsular polysaccharides of lower molecular weight, e.g. 10,000 to 20,000 on average, polysaccharides as purified may be submitted to fragmentation. To this end, conventional methods are available; e.g. WO 93/7178 describes a fragmentation method by reductive oxidation.

The hydroxyl, carboxyl or amino groups of the polysaccharide that are involved in the linkage, may be native functional groups. Alternatively, they may have been introduced artificially by specific treatment.

Amino groups may have been created upon controlled acidic or basic hydrolysis of native N-acyl groups e.g., N-acetyl groups.

Functional groups including hydroxyl, carboxyl, amino groups and others (although amino groups are preferred), may also have been introduced upon derivatization with a spacer moiety bound to the native amino, hydroxyl or carboxyl groups, these two latter being preferred to this end. Typically, the spacer is a bifunctional molecule being able to react at one end with the native hydroxyl, carboxyl or amino groups of the polysaccharide and at the other end with the linker. Thus the spacer provides for a functional group including, but not limited to, hydroxyl, carboxyl and amino groups. Another useful functional group that may also be introduced by the spacer is a thiol group, as further detailed hereinafter.

Functional groups other than those already cited may also have been introduced upon specific treatment. For example, aldehyde groups may have been introduced all along the polysaccharide chain by periodate treatment that cleaves a carbon-carbon link between two carbon atoms bearing vicinal hydroxyl groups. A periodate treatment is preferably achieved on a polysaccharide, the chain of which is not susceptible to be cleaved by such a treatment e.g., from *S. mutans*.

When aldehyde groups are introduced all along the chain for conjugation purposes, the linker that is used, exhibits an amino group.

Compounds to be used as spacers or linkers are further defined hereinafter. It is however right now indicated that the linker is a bifunctional molecule having an appropriate length so that the peptide and polysaccharide moieties do not interfere with each other e.g. when presented to the immune system. The linker moiety is advantageously linked to the cysteine residue of the peptide through a disulphure bridge or a thio ether bound and to hydroxyl groups of the polysaccharide through an ether or ester bound, to amino groups through a amide or carbamate bound, to carboxyl groups through an ester, amide or carbamate bound, or to aldehyde groups through a reduced imine bound.

The nature and intensity of the immune response that may be elicited by a vaccinal conjugate of the invention, may be greatly influenced by the ratio peptide polysaccharide. It is essential that B-epitopes present in the polysaccharide and T-dependent epitopes carried by the peptide be available and correctly presented to the immune system. Thus, both types of epitopes shall be present in sufficient and balanced amount so as to avoid for example steric hindrance of the polysaccharide epitopes by the peptide moieties. In order to optimize the immune response, it is indicated that a ratio 1 mole of peptide per 1 to 50 moles of repeat units is suitable. Preferably, this ratio is of 1 mole of peptide per 3 to 30 moles of repeat units; more preferably, this ratio is of 1 mole of peptide per 5 to 20 moles of repeat units.

Conjugates of the invention are in particular useful in the vaccinal field to elicit a protective long term immune response against a pathogenic microorganism from which the immunogenic polysaccharide is derived.

Therefore, the invention also provides for a pharmaceutical composition comprising a therapeutically or prophylactically effective amount of a conjugate of the invention, together with a pharmaceutically acceptable diluent or carrier. Such a composition may be conventionally prepared. It may also contain other ingredients such as an adjuvant, e.g. an aluminium compound. Suitable aluminium compounds include aluminium hydroxide or aluminium phosphate. In a preferred embodiment, it is not necessary to use an adjuvant to enhance the immunogenicity of a conjugate of the invention. A composition according to the invention may be administered by any conventional route in use in the vaccine field. The choice of the administration route depends upon a number of parameters such as the adjuvant used.

A further aspect of the present invention relates to a process for conjugating a peptide having at least six amino acid residues, at least one of which being a cysteine residue to a polysaccharide chain i.a., an immunogenic polysaccharide chain, comprising at least four repeat units, which comprises coupling the peptide to a linker through the thiol group of the cysteine residue and coupling the polysaccharide to said linker through (a) the native amino, hydroxyl or carboxyl groups of the polysaccharide chain or (b) amino groups created upon hydrolysis of the native N-acyl groups of the polysaccharide chain or (c) functional groups introduced on the polysaccharide chain upon derivatization with a spacer moiety bound to the native amino, hydroxyl or carboxyl groups of the polysaccharide chain.

It is preferred to first react the linker with the polysaccharide or a derivatized polysaccharide which provides for an activated polysaccharide, i.e. a polysaccharide carrying the linker molecule providing a functional group for the coupling to the peptide. In a second step, this activated polysaccharide is reacted with the peptide where the functional group of the linker, i.e. $R_1$, reacts with the thiol group of a cysteine residue of the peptide.

Said otherwise, it is provided a process for conjugating a peptide containing a cysteine residue to a polysaccharide i.a., an immunogenic polysaccharide, composed of at least four repeat units, said process comprising either:

(i) activating a polysaccharide with a bifunctional linker able to react with a thiol group so that an activated polysaccharide is obtained, wherein a plurality of linker moieties are introduced at random along the polysaccharide chain by covalent attachement, and (ii) reacting the activated polysaccharide obtained in step (i) with the peptide so that a conjugate is obtained, wherein peptide entities are covalently attached to said linker moieties through their cysteine residue; or (iii) activating the peptide with a bifunctional linker able to react with a thiol group, and (iv) reacting the activated peptide obtained in (iii) with the polysaccharide so that a conjugate is obtained, wherein a plurality of activated peptide entities are introduced at random all along the polysaccharide chain by covalent attachement.

A preferred process is according to steps (i) and (ii).

An advantageous process according to the invention comprises reacting the polysaccharide with a bifunctional linker under conditions that allow the introduction of linker moieties onto the polysaccharide in a sufficient amount so that in step (ii) of the process, a conjugate is produced, which contains one peptide mole per 1 to 50 moles of repeat units, preferably one peptide mole per 3 to 30 moles of repeat units, more preferably one peptide mole per 5 to 20 moles of repeat units. In a similar manner, the alternative process comprises reacting the polysaccharide with an activated peptide under conditions that allow the introduction of activated peptide moieties onto the polysaccharide in a sufficient amount so that in step (iv) of the process, a conjugate is produced having the features recited hereinabove.

An advantageous linker is of formula (I) R1-A—R2, wherein R1 is a functional group able to react with a thiol group, A is an aromatic or preferably, an aliphatic chain e.g., a carbon chain, substituted or not, and R2 is a functional group able to react with a functional group of the polysaccharide.

Chain A shall be neither too short (to avoid steric hindrance) nor too long (to avoid interference with the immunogenic parts). Thus, chain A comprises from 1 to 12, preferably from 3 to 8 carbon atoms and is more preferably selected from $C_2$–$C_8$ alkylene, phenylene, $C_7$–$C_{12}$ aralkylene, $C_2$–$C_8$ alkyl, phenyl, $C_7$–$C_{12}$ aralkyl, $C_6$ alkanoyloxy and benzylcarbonyloxy, wherein alkyl, phenyl, alkylene and phenylene can be substituted or not.

R1 is preferably a thiol group; an α, β—unsaturated carbonyl or imidyl group; an acylhalogen or an alkylhalide, wherein the halogen atom is Br, Cl or I. In a more preferred embodiment, R1 is an α, β—unsaturated carbonyl or imidyl group, especially a maleimidyl group.

R2 is the functional group of the linker which provides for the link to the polysaccharide. Thus, R2 is a group that can react with i.a. amino, carboxyl, hydroxyl or aldehyde groups. R2 is preferably selected from amino, carbamoyl, amino carbamoyl, carboxyl, hydroxyl, succinimidyl e.g. N-hydroxy succinimidyl and sulfosuccinimidyl e.g. N-hydroxy sulfosuccinimidyl. If the linker is reacted with amino groups, R2 is preferably a carboxyl, succinimidyl e.g.

N-hydroxy succinimidyl and sulfosuccinimidyl e.g. N-hydroxy sulfosuccinimidyl. If the linker is reacted with hydroxyl or carboxyl or aldehyde groups, R2 is preferably an amino group or a chemical moiety carrying an amino group, for example R2 is an hydrazide group i.e., $NH_2$—NH—CO—.

Compounds being useful as linker include succinimidyl-4-(N-maleiimidomethyl) cyclohexan-1-carboxylate, N-succinimidyl-4-(4-maleiimidophenyl) butyrate, N-succinimidyl-4-maleiimido-butyrate, N-succinimidyl-3-maleiimido-benzoate.

As explained hereinabove, the polysaccharide may be derivatized with a spacer prior to conjugation. Thus, the polysaccharide may. be reacted first with a spacer of formula (II) R3-B—R4, wherein R3 is a functional group able to react with amino, carboxyl or hydroxyl groups, B is an aromatic or aliphatic chain, and R4 is a functional group able to react with the R2 group of the linker used in further conjugation step.

Chain B may be a carbon chain, preferably carbonyl, C1–C12 alkyl or alkylene or dicarbonyl.

Preferably, R3 and R4 independently are an amino group or a chemical moiety carrying an amino group, for example an hydrazide group i.e. $NH_2$—NH—CO—.

Compounds useful as spacer in the present invention include cysteamine, cysteine, diamines e.g. diaminohexane, adipic acid dihydrazide (ADH), urea, semicarbazide, and cystamine.

When cysteamine or cysteine is used as a spacer, thiol groups are introduced onto the polysaccharide. In this case, useful linkers to be used in combination include for example, bis maleimidyl compounds such as bis maleimido hexane.

In order to obtain a conjugate exhibiting an appropriate peptide: polysaccharide ratio as described hereinabove, it is within the knowledge of a man skilled in the art to test an adjust the reaction conditions e.g., the concentration of the reagents involved in the derivatization and/or activation steps. Further guidance is offered as follows:

When amino groups of the polysaccharide are reacted, the reaction is preferably achieved in the presence of a carbodiimide compound e.g., (3-dimethylaminopropyl)-3-ethyl carbodiimide hydrochloride (EDAC) at a pH of 4 to 7, provided that the functional group of the linker or spacer that is involved in the reaction, is carboxyl.

When carboxyl groups of the polysaccharide are reacted, the reaction is preferably achieved in the presence of a carbodiimide compound as above, provided that the functional group of the linker or spacer that is involved in the reaction, is an amino group.

The molar ratio of polysaccharide repeat units: carbodiimide is advantageously in the range of 0.1 to 2, preferably in the range of 0.1 to 1, more preferably in the range of 0.2 to 0.6. As may be easily understood, by adjusting this ratio, the amount of peptide moieties per repeat units can be controlled.

When amino groups of the polysaccharide are reacted with succinimidyl or sulfosuccinimidyl, the reaction is avantageously achieved at pH from 6 to 9, preferably about 7.5. Succinimidyl groups react only with amino groups. When appropriate experimental conditions are used (e.g., excess of linker), the reaction is almost immediate i.e., within about 5 min. If the polysaccharide used in the reaction is a native polysaccharide bearing amino groups, the only possibility to control the amount of substitution by succinimidyl groups is to, use adverse experimental conditions (otherwise the reaction immediately occurs and all the amino groups are substituted), such as an increased dilution of the reaction medium or a low linker amount. This allows to adjust the ratio of peptide to repeat unit in the appropriate range. If hydrolysis or derivatization is used to introduce amino groups on the polysaccharide, this ratio may be easily controlled by controlling the appearance of the amino groups onto the polysaccharide.

When hydroxyl groups of the polysaccharide are reacted, the reaction is preferably achieved in the presence of a cyanogen compound; at pH from 8 to 12, if this compound is cyanogen bromide; or at pH from 6 to 10, preferably from 6 to 8, if the compound is 1-cyano-4-dimethyl aminopyridinium tetrafluoroborate. The molar ratio of polysaccharide repeat units: cyanogen compound is advantageously in the range of 0.1 to 3, preferably in the range of 0.1 to 2.

When aldehyde groups present along the polysaccharide chain are reacted, the reaction is preferably carried out in the presence of cyanoborohydride e.g., $NaCNBH_3$ at pH from 6.5 to 8.

By carrying out the method of the invention, a conjugate is obtained wherein polysaccharide and peptide moieties are bound via a linker moiety or a combination of both spacer and linker, wherein the linker or the linker/spacer moiety has an optimal length and wherein the polysaccharide-peptide linkage is stable. Moreover, a conjugate is obtained, wherein the ratio of peptide to repeat-units of polysaccharide is optimal for immunization purposes.

The invention is further illustrated as follows:

EXAMPLE 1

Preparation of a Synthetic 105mer Peptide Having the Following Sequence

Cys Leu Tyr Tyr Lys Asn Tyr Arg Tyr Tyr Ala Leu Lys Ser Gly Gly Ser Val Asn Ala Pro Met Pro Glu Asn Gly Gln Thr Glu Asn Asn Asp.Trp Ile Leu Met Gly Ser Thr Gln Glu Glu Ala Lys Lys Asn Ala Met.Asn His Lys Asn Asn Gln Arg Ile Ser Gly Phe Ser Gly Phe Phe Gly.Glu Glu Asn Gly Lys Gly His Asn Gly Ala Leu Asn Leu Asn Phe Asn.Gly Lys Ser Ala Gln Asn Arg Phe Leu Leu Thr Gly Gly Thr Asn Leu.Asn Gly Lys Ile Ser Val Thr Gln Gly

The peptide was synthesized using a FastMoc chemistry with an automated peptide synthesizer (model 431A, Applied Biosystems). The solid phase was a Rink resin (0.13 mM TentaGel S RAM Spezial, 0.15 mM $g^{-1}$, Rapp Polymere, Tubingen, Germany) which yields a C-terminal amide capped peptide. Synthesis uses Fmoc (9-fluorenylmethyloxycarbonyl) protected amino acids with O-t-butyl- (for the aspartic acid, glutamic acid, serine, threonine and tyrosine carboxyl or hydroxyl group); trityl- (for the histidine, asparagine and glutamine amino or imino group); t-butyloxycarbonyl- (for the lysine amino group); or PMC (pentamethylchroman-6-sulfonyl) (for the arginine imino group) side protection.

Activation and coupling were achieved in the presence of 2-(1H-benzotriazol-1-yl)-3,3,3-tetramethyluronium hexafluorophosphate (HBTU)/diisopropylethylamine. At cycles 1–2, 4, 10–13, 17, 27, 32, 49, 59, 66, 75–78, 84–85, 88, 96–97 and 104–105, double coupling was performed and free amino groups were blocked by acetylation with acetic anhydride. After the last cycle, the peptide was deprotected with piperidine and the final product was N-terminally acetylated using acetic anhydride.

Side-chain deprotection and cleavage from the resin support were carried out with 2.1% (v/v) 1,2-ethanedithiol, 4.2% (v/v) thioanisol, 4.2% (v/v) water, 6.2.% phenol (v/v) and 83% (v/v) trifluoroacetic acid (TFA) for 3 hours at room temperature. The resin was removed by filtration and triethylsilane was added dropwise until the solution was colourless. The solution was then incubated 3 hours at room temperature. 360 mg crude peptide was recovered after precipitation with t-butylmethylether followed by centrifugation and lyophilisation. 130 mg of the crude peptide was dissolved in 40 ml 50 mM ethylmorpholine, pH 8.3 containing 50 mM dithiothreitol and incubated overnight at room temperature. pH was adjusted to 3.5 with 10% TFA and the peptide was purified by reverse phase HPLC (Pep-S, C2/C18, 100 Å pore size, 12 µm 22.5 mm×25 cm, Pharmacia) using a gradient (25 to 45% (v/v) of acetonitrile, 0.1% TFA (10 ml min$^{-1}$, gradient of 0.33% min$^{-1}$. The peptide eluted as one peak at about 25% acetonitrile, and the peak was lyophilized (73 mg) before further use. An analysis by HPLC and mass spectrometry showed that over 65% of the final product corresponded to the desired sequence. The N-terminal sequence was confirmed by N-terminal Edman sequencing of the sample removed before N-terminal acetylation.

EXAMPLE 2

*N. meningitidis* Serogroup C Polysaccharide-peptide Conjugate

A dry powder of capsular polysaccharide from *Neisseria meningitidis* serogroup C, hereinafter referred to as polysaccharide C, was obtained by an extraction process as described by Gotschlich et al, J. Exp. Med. (1969) 129: 1349. One hundred mg of polysaccharide C were dissolved in 0.2 M NaCl to a final concentration of 11.1 mg/ml (solution A). In parallel, a solution of 0.2 M adipic acid dihydrazide (ADH) in 0.2 M NaCl was prepared (solution B). A 0.5 M solution of ethyl dimethyl aminopropyl carbodiimide (EDAC) in 0.2 M NaCl was also prepared (solution C). Nine ml of solution A, 10 ml of solution B and 1 ml of solution C are mixed together to give a preparation containing 5 mg/ml of polysaccharide C, 0.125 M ADH and 0.025 M EDAC. 0.1 M HCl was added to adjust pH to 6.5; this pH was maintained during the entire reaction period of 45 minutes. The temperature was about 20° C.

Reaction was stopped by 40 µl 0.1 N NaOH which raised pH to 7.1. The reaction mixture was dialyzed against 0.5 M NaCl, 10 mM phosphate and then water and subsequently lyophilized.

The size of the derivatized polysaccharide C was controlled on an HPLC exclusion column TSK 4000 (manufacturer Tosohaas). The results demonstrated that no depolymerization had occurred in the course of the derivatization.

During the derivatization, about 3.4% of repeat units were derivatized with an NH$_2$ group.

The lyophilized product was dissolved in 0.02 M phosphate buffer, pH 7, to a concentration of 6.25 mg/ml and degassed. N-(γ-maleimidobutyryloxy) succinimide ester (GBMS) was dissolved in dimethylsulfoxide (DMSO) under nitrogen at a concentration of 25 mg/ml and then added to derivatized polysaccharide C in equal amount. The reaction mixture was stirred for 90 minutes at room temperature under nitrogen. The activated polysaccharide C was purified by Sephadex G50 exclusion column chromatography. The excluded fraction was recovered and concentrated to about 7.5 mg/ml by ultrafiltration (30K Amicon membrane). The concentrated solution was degassed.

Twenty mg of peptide as obtained in Example 1 was dissolved in water at a concentration of 10 mg/ml under nitrogen. One and half ml of the peptide solution was added to 1.2 ml of the preparation containing the activated polysaccharide C, so that the ratio (maleiimido residues)/(thiol residues) amounts 2. The reaction mixtures were maintained over night under stirring at room temperature. Then the unreacted maleiimido residues were inactivated by adding 0.010 ml mercaptoethanol.

The conjugated product was purified on a 4BCL Sepharose column. The eluted fractions were assayed for the presence of saccharides (sialic acid) and peptides. Fractions responding positively in both assays were pooled.

The amount of sialic acid residues was determined according to the dosage method described in Svennerholm L., Biochem. Biophys. Acta (1957) 24: 604, and the amount of peptide was determined according to the method of Lowry et al, J. Biol. Chem. (1951) 193: 265. It was shown that the ratio (peptide)/(repeat units of polysaccharide C) mole/mole was 1:18 (corresponding to a ratio weight/weight of 1.8:1).

EXAMPLE 3

*S. Pneumoniae* Polysaccharide-peptide Conjugate

A dry powder of capsular polysaccharide from *Streptococcus pneumoniae* type 4, hereinafter referred to as Pneumo 4 polysaccharide, is obtained by an extraction process as described in patent application WO 82/01995 "Procédé de purification de polyosides de *Streptococcus pneumoniae* et vaccins a base de polyosides ainsi purifiés". One hundred mg of Pneumo 4 polysaccharide were dissolved in 0.2 M NaCl to a final concentration of 11.1 mg/ml (solution A). In parallel, a solution of adipic acid dihydrazide (ADH) in 0.2 M NaCl was prepared in a concentration of 0.25 M (solution B). A solution of ethyl dimethyl aminopropyl carbodiumide (EDAC) in 0.2 M NaCl was also prepared at a concentration of 0.5 M (solution C). Nine ml of solution A, 10 ml of solution B and 1 ml of solution C are mixed together to give a preparation containing 5 mg/ml of Pneumo 4 polysaccharide, 0.125 M ADH and 0.025 M EDAC. 1 N HCl was added to pH 4.9; this pH was maintained during the entire reaction period of 30 minutes. The temperature was about 25° C.

Reaction was stopped by 0.28 ml 1 N NaOH. The pH was increased to 7.5. The reaction mixture was dialyzed against 0.5 M NaCl and then water and subsequently lyophilized.

The size of the derivatized Pneumo 4 polysaccharide was controlled on an HLPC exclusion column TSK 4000 (manufacturer Tosohaas). No depolymerization occurred in the course of the derivatization.

During the derivatization, about 8.2% of repeat units of the Pneumo 4 polysaccharide were derivatized with a —NH$_2$ group.

Lyophilized product was dissolved in 0.05 M NaCl at a concentration of 2.76 mg/ml and degassed. N-(γ-maleimidobutyryloxy) succinimide ester (GBMS) was dissolved in dimethylsulfoxide (DMSO) under nitrogen at a concentration of 25 mg/ml. 1.75 ml of the GMBS solution were added to 16 ml of the polysaccharide solution under nitrogen. The reaction mixture was left under stirring for 5 hours at room temperature under nitrogen. The activated Pneumo 4 polysaccharide was purified on an exclusion column Sephadex G50. The excluded fraction was recovered and concentrated to about 7 mg/ml on a 30K membrane (Amicon). The concentrated solution was degassed.

Twenty mg of peptide as obtained in Example 1 were dissolved in 0.1 M NaCl, 0.01 M phosphate buffer pH 7.5, at a concentration of 4.6. mg/ml under nitrogen. On the one hand, 2.2 ml of the peptide solution were added to 1.25 ml of the preparation containing the activated Pneumo 4 polysaccharide, so that the ratio (maleiimidyl residues)/(thiol groups) equalled 1 (Pneumo 4-peptide-1 conjugate). Reaction mixtures were maintained 6 hours under stirring at room temperature under nitrogen, then overnight at +4° C. Then the unreacted maleiimidyl residues were inactivated by adding 0.005 ml mercaptoethanol to each reaction mixture.

The conjugates were purified on a Sepharose 4BCL column. The eluted fractions were assayed for the presence of sugars and peptides. Fractions responding positively in both assays were pooled.

The amount of sugar was determined according to the dosage method described in Dubois et al, Anal. Chem. (1956) 3: 350, and the amount of peptide was determined according to the method of Lowry et al, J. Biol. Chem. (1951) 193: 265. The ratio (repeat units of (peptide/polysaccharide) mole/mole is 1:30 for Pn 4-peptide-1 conjugate (corresponding to a ratio w/w of 0.4:1).

EXAMPLE 4

N. meningitidis Serogroup A polysaccharide-peptide Conjugate

A dry powder of capsular polysaccharide from Neisseria meningitides serogroup A, referred to as polysaccharide A in the following, is obtained by an extraction process as described by Gottschlich et al, J. Exp. Med. (1969) 129: 1349. One hundred mg of polysaccharide A were dissolved in water to a final concentration of 5 mg/ml (solution A). In parallel, a solution of cyanogen bromide (CNBr) in water was prepared in a concentration of 67 mg/ml (solution B). A solution of adipic acid dihydrazide (ADH) in 0.5 M NaHCO$_3$ was also prepared at a concentration of 150 mg/ml (solution C). Tweenty of solution A and 0.75 ml of solution C were mixed together to give a preparation with a ratio polysaccharide/CNBr weight/weight that amounts 1. 0.1 N NaOH was added to a pH of 10.8; this pH was maintained during the entire reaction period of 60 minutes. The temperature was about 20° C.

Then pH was decreased to 8.5 by adding 0.15 ml 0.1 N HCl. 1.Seventeen ml of solution C were added so that the ratio ADH/polysaccharide weight/weight amounts 3.5. The pH was maintained during 15 minutes. Then the reaction mixture was left overnight under stirring at +4° C. 0.1 ml 1 N HCl were added to decrease the pH to 7. The reaction mixture was dialyzed against 0.5 M NaCl and then water and subsequently lyophilized.

The size of the derivatized polysaccharide A was controlled on a HLPC exclusion column TSK 4000 (manufacturer Tosohaas). No depolymerization occurred in the course of derivatization.

During the derivatization, about 2.5% of repeat units of polysaccharide A were derivatized with a —NH$_2$ group.

Then the process of Example 2 were used to activate the derivatized polysaccharide A and to conjugate the activated polysaccharide A to the peptide as obtained in Example 1.

EXAMPLE 5

Immunogenicity Studies with the N. meningifidis Serogroup C Conjugate as Obtained in Example 2

The utility of the peptide of Example 1 as a carrier in a polysaccharide conjugate is demonstrated as follows.

Six-week old NMRI mice received via the sub-cutaneous route one of the following compositions in a volume of 0.5 ml (each injection) and via the intraperitoneal route, in case an adjuvant was used:

a) 5 μg polysaccharide C (without peptide) at days 1, 15 and 29, in the absence of adjuvant;

b) 5 μg polysaccharide C (without peptide) together with complete Freund's adjuvant at day 1, and at days 15 and 29 together with incomplete Freund's adjuvant;

c) 5 μg polysaccharide C and 9 μg peptide together with complete Freund's adjuvant at day 1, and at days 15 and 29 together with incomplete Freund's adjuvant;

d) the conjugate obtained in Example 2 containing 1 μg polysaccharide C and 1.8 μg peptide at days 1, 15 and 29 in the absence of adjuvant;

(e) the conjugate obtained in Example 2 containing 5 μg polysaccharide C and 9 μg peptide at days 1, 15 and 29 in the absence of adjuvant;

(f) the conjugate obtained in Example 2 containing 5 μg polysaccharide C and 9 μg peptide together with complete Freund's adjuvant at day 1, and at days 15 and 29 the conjugate obtained in Example 2 together with incomplete Freund's adjuvant; and g) a conjugate of 5 μg polysaccharide C together with diphtheria anatoxin (DT).

On days 15, 29 and 43 (calculated from the day of the first immunisation), a sample of blood is collected and the antipolysaccharide C antibodies are titrated by ELISA. The results are summarized in the following table.

TABLE 1

| Compound injected | Dose of polysaccharide injected (μg) | Dose of peptide injected (μg) | Day after immunisation | Sample of blood collected on day | Antipolysaccharide antibody titer (ELISA unit) |
|---|---|---|---|---|---|
| (a) | 5 | | 1 | 15 | 10 |
| | | | 15 | 29 | 32 |
| | | | 29 | 43 | 115 |
| (b) | 5 | | 1 | 15 | 22 |
| | | | 15 | 29 | 39 |
| | | | 29 | 43 | 74 |
| (c) | 5 | 9 | 1 | 15 | 24 |
| | | | 15 | 29 | 34 |
| | | | 29 | 43 | 47 |
| (d) | 1 | 1.8 | 1 | 15 | 32 |
| | | | 15 | 29 | 1052 |
| | | | 29 | 43 | 630 |
| (e) | 5 | 9 | 1 | 15 | 56 |
| | | | 15 | 29 | 321 |
| | | | 29 | 43 | 516 |
| (f) | 5 | 9 | 1 | 15 | 1006 |
| | | | 15 | 29 | 2854 |
| | | | 29 | 43 | 2492 |
| (g) | 5 | | 1 | 15 | 13 |
| | | | 15 | 29 | 1197 |
| | | | 29 | 43 | 1531 |

The antibody response to non-conjugated polysaccharide C is extremely weak in each case and does not increase over time, whereas the response to polysaccharide C conjugated to either DT or the peptide is satisfactory. With the conjugate of the present invention a booster effect is obtained after the second injection, being an indication for a persistent immune response. The response of the conjugate polysaccharide C—peptide is equivalent to the response obtained with the conjugate of polysaccharide C—DT.

EXAMPLE 6

Immunogenicity Studies with the S. pneumoniae Conjugate as Obtained in Example 3

The conjugate prepared in Example 3 with a ratio (w/w) of peptide to polysaccharide of 0.4:1 (corresponding to a ratio of peptide per repeat units of 1:30 (mole/mole)) was tested in mice using the protocol of Example 5. It was immunogenic in mice in the presence of adjuvant and resulted in a booster effect after the second injection. The results are to be seen hereinafter in Table 2.

TABLE 2

| Compound injected | Dose of polysaccharide injected (μg) | Dose of peptide injected (μg) | Day after immunisation | Sample of blood collected on day | Anti-polysaccharide antibody titer (ELISA unit) |
|---|---|---|---|---|---|
| Pneumo type 4 PS + adjuv. | 5 | | 1 15 29 | 15 29 43 | <10 <10 <10 |
| Pneumo type 4 PS + peptide + adjuv. | 5 | 1.9 | 1 15 29 | 15 29 43 | ~18 ~24 <10 |
| Conj. Pn4-peptide-1 + adjuv. | 5 | 1.9 | 1 15 29 | 15 29 43 | ~61 458 2601 |
| Saline | | | 1 15 29 | 15 29 43 | <10 <10 <10 |

What is claimed is:

1. A polysaccharide-peptide conjugate wherein the polysaccharide is immunogenic, which comprises:
   (i) a peptide moiety having at least six amino acid residues, at least one of which being a cysteine residue;
   (ii) a polysaccharide chain comprising at least four repeat units; and
   (iii) a linker moiety bound to the thiol group of the cysteine residue and bound to (a) the native amino, hydroxyl or carboxyl groups of the polysaccharide chain or (b) amino groups created upon hydrolysis of the native N-acyl groups of the polysaccharide chain or (c) functional groups introduced on the polysaccharide chain upon derivatization with a spacer moiety bound to the native amino, hydroxyl or carboxyl groups of the polysaccharide chain.

2. A conjugate according to claim 1, wherein the peptide contains from six to two hundred amino acid residues, comprising at least one cysteine residue.

3. A conjugate according to claim 2, wherein the peptide contains from ten to one hundred fifty amino acid residues, comprising at least one cysteine residue.

4. A conjugate according to claim 3, wherein the peptide contains from fifteen to one hundred amino acid residues, comprising at least one cysteine residue.

5. A conjugate according to claim 4, wherein the peptide contains from twenty to fifty amino acid residues, comprising at least one cysteine residue.

6. A conjugate according to claim 1, wherein the cysteine residue is located at the N- or C-terminal end of the peptide moiety.

7. A conjugate according to claim 1 or 2, wherein the cysteine residue is located at the N- or C-terminal end of the peptide moiety.

8. A conjugate according to claim 1 or 2, wherein the polysaccharide is a native polysaccharide selected from the O-specific chain of bacterial lipopolysaccharides, detoxified lipopolysaccharides, and capsular polysaccharides.

9. A conjugate according to claim 1 or 2, wherein the polysaccharide is derived from a native polysaccharide comprising N-acetyl groups, by controlled acidic or basic hydrolysis.

10. A conjugate according to claim 9, wherein the polysaccharide is derived from a native selected from a capsular polysaccharide.

11. A conjugate according to claim 1 or 2, wherein the polysaccharide is composed of 4 to 3000 repeat units.

12. A conjugate according to claim 11, wherein the polysaccharide is composed of 4 to 1000 repeat units.

13. A conjugate according to claim 12, wherein the polysaccharide is composed of 7 to 700 repeat units.

14. A conjugate according to claim 1 or 2, which contains from one mole peptide for fifty moles of repeat units (1:50) to one mole peptide for one mole of repeat units (1:1).

15. A conjugate according to claim 14, which contains from one peptide mole for thirty moles of repeat units (1:30) to one peptide mole for three moles of repeat units (1:3).

16. A conjugate according to claim 15, which contains from one peptide mole for tweenty moles of repeat units (1:20) to one peptide mole for five moles of repeat units (1:5).

17. A pharmaceutical composition comprising a conjugate according to claim 1, together with a pharmaceutically acceptable diluent or carrier.

18. A composition according to claim 17, which does not comprise any adjuvant.

19. A process for conjugating a peptide having at least six amino acid residues, at least one of which being a cysteine residue to a polysaccharide chain, comprising at least four repeat units, which comprises coupling the peptide to a linker through the thiol group of the cysteine residue and coupling the polysaccharide to said linker through (a) the native amino, hydroxyl or carboxyl groups of the polysaccharide chain or (b) amino groups created upon hydrolysis of the native N-acyl groups of the polysaccharide chain or (c) functional groups introduced on the polysaccharide chain upon derivatization with a spacer moiety bound to the native amino, hydroxyl or carboxyl groups of the polysaccharide chain.

20. The process according to claim 19 wherein said polysaccharide chain is an immunogenic polysaccharide chain.

* * * * *